US00PP11360P

United States Patent [19]

Clucas

[11] Patent Number: Plant 11,360

[45] Date of Patent: Apr. 25, 2000

[54] BRACHYCOME PLANT NAMED 'JUMBO MISTY LILAC'

[75] Inventor: Evan Philip Clucas, Wandin North, Australia

[73] Assignee: Outback Plants Pty. Ltd., The Patch, Australia

[21] Appl. No.: 09/177,287

[22] Filed: Oct. 22, 1998

[51] Int. Cl.[7] ..... A01H 5/00

[52] U.S. Cl. ..... Plt./263

[58] Field of Search ..... Plt./263

*Primary Examiner*—Howard J. Locker

*Assistant Examiner*—Kent L. Bell

*Attorney, Agent, or Firm*—C. A. Whealy

[57] ABSTRACT

A new and distinct cultivar of Brachycome plant named 'Jumbo Misty Lilac', characterized by its upright and spreading growth habit; freely branching plant habit; numerous large inflorescences with light purple ray florets that fade to lighter purple with development; and erect peduncles that hold inflorescences above the foliage.

2 Drawing Sheets

BACKGROUND OF THE INVENTION

The present invention relates to a new and distinct cultivar of Brachycome plant, botanically known as *Brachycome segmentosa* Hybrid and referred to by the cultivar name 'Jumbo Misty Lilac'.

The new Brachycome was discovered by the Inventor in a group of seedling progeny from a cross of unidentified selections of *Brachycome segmentosa* Hybrid in an outdoor area in Wandin North, Victoria, Australia.

Asexual reproduction of the new Brachycome by terminal cuttings taken in a controlled environment in Wandin North, Victoria, Australia, has shown that the unique features of this new Brachycome are stable and are reproduced true to type in successive generations.

SUMMARY OF THE INVENTION

The new Brachycome has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Jumbo Misty Lilac' and distinguish 'Jumbo Misty Lilac' as a new and distinct cultivar:

1. Upright and spreading growth habit.

2. Freely branching plant habit.

3. Numerous large inflorescences with light purple ray florets that fade to lighter purple with development.

4. Erect peduncles that hold inflorescences above the foliage.

BRIEF DESCRIPTION OF THE PHOTOGRAPHS

The accompanying colored photographs illustrate the overall appearance of the new Brachycome, showing the colors as true as it is reasonably possible to obtain in colored reproductions of this type. The photograph on the first sheet comprises a view from above of a typical potted plant of 'Jumbo Misty Lilac'. The photograph on the second sheet comprises a close-up view of typical inflorescences of 'Jumbo Misty Lilac'. Floret and foliage colors in the photographs may appear different from the actual colors due to light reflectance.

DETAILED BOTANICAL DESCRIPTION

The following observations, measurements, values, and comparisons describe plants grown in Victoria, Australia, under outdoor conditions with day temperatures ranging from 12 to 40° C., night temperatures ranging from 6 to 25° C., and light levels ranging from 5,000 to 9,000 footcandles. Color references are made to The Royal Horticultural Society Colour Chart except where general terms of ordinary dictionary significance are used.

Botanical classification:

*Brachycome segmentosa* Hybrid cultivar 'Jumbo Misty Lilac'.

Parentage:

*Male or pollen parent.*—Unidentified selection of *Brachycome segmentosa* Hybrid.

*Female or seed parent.*—Unidentified selection of *Brachycome segmentosa* Hybrid.

Propagation:

*Type.*—By cuttings.

*Time to initiate and develop roots.*—Summer: About 10 to 20 days at temperatures of 25° C. Winter: About 15 to 30 days at temperatures of 20° C.

*Rooting habit.*—Fine, fibrous and freely branching.

Plant description:

*General appearance.*—Upright and spreading, flat to rounded herbaceous plant with erect peduncles. Suitable for 15 to 20-cm containers. To produce a 15-cm finished flowering plant from rooted cuttings, 10 to 14 weeks are required depending on temperature and light level.

*Plant height.*—About 25 to 45 cm from soil level to top of inflorescences.

*Plant diameter or spread.*—About 30 to 50 cm.

*Branching.*—Freely branching, numerous lateral branches develop after removal (pinching) of the terminal apex.

*Growth rate/vigor.*—Moderate.

*Stem description.*—Lateral branch length: About 1.8 to 9.2 cm. Lateral branch diameter: About 1 to 2 mm. Internode length: About 0.2 to 1.8 cm. Texture: Young, slightly pubescent; older, glabrous. Color: 146A to 146B.

*Foliage description.*—Arrangement: Alternate, single. Quantity: About 14 to 27 per lateral branch. Shape: Narrowly spatulate in outline, lobed and sometimes toothed. Apex: Narrowly lobed with each segment usually having two to three teeth. Base: Sessile, somewhat clasping. Length: About 1.9 to 4.4 cm. Width: About 0.5 to 1.6 cm. Margin: Three to seven-lobed, often lacking teeth. Texture: Smooth, glabrous. Color: Young leaves, upper surface: 137A. Young leaves, lower surface: 137B. Fully expanded leaves, upper surface: 136B; venation, 147C. Fully expanded leaves, lower surface: 136B; venation, 147C.

Flowering description:

*Inflorescence.*—Single daisy-type composite inflorescence form. Florets arranged acropetally on a capitulum. Inflorescences last on the plant for about 6 to 12 days and about 7 to 10 days as a fresh cut flower. Self-cleaning.

*Natural flowering season.*—Natural flowering season is spring to fall; flowering continuous during this period.

*Response time.*—About 5 to 8 weeks.

*Quantity of inflorescences.*—About one to four per lateral branch with numerous inflorescences per plant.

*Inflorescence diameter.*—About 2.8 to 3.9 cm.

*Inflorescence depth (height).*—About 1 cm.

*Disc diameter.*—About 1.5 to 1.8 cm.

*Inflorescence aspect.*—Flat.

*Rate of inflorescence opening.*—About 6 to 10 days.

*Fragrance.*—Very faint, honey-like.

*Inflorescence buds.*—Shape: Spherical. Length: About 7 mm. Diameter: About 6 to 7 mm. Color: 191B to 193B.

*Ray florets.*—Quantity: About 25 to 36 florets per inflorescence arranged in one to two rows. Shape: Narrowly oblanceolate. Apex: Blunt, rounded. Base: Attenuate. Margin: Entire. Aspect: Flat. Length: About 1.1 to 1.7 cm. Width: About 2 to 3 mm. Texture: Smooth, glabrous, thin. Color: When opening, upper surface: 80A to 80B. When opening, lower surface: 80B. Mature, upper surface: 76C to 76D. Mature, lower surface: 76A to 76D.

*Disc florets.*—Shape: Tubular with five lobes. Length: About 3 mm. Width: About 1 mm. Texture: Sparse glandular hairs. Color: Immature: 154A. Mature: 7A. Number of disc florets per inflorescence: Numerous.

*Peduncle.*—Length: About 8.9 to 16.5 cm. Strength: Initially somewhat flexible becoming fairy rigid; erect. Texture: Smooth, glabrous. Color: 137A.

*Involucral bracts.*—Arrangement: Imbricate. Quantity: About 13 to 21 per inflorescence. Shape: Broadly oblong. Apex: Fringed. Margin: Entire to faintly fringed. Texture: Somewhat fleshy. Color: 138A with brownish apex, 182B. Mature, upper surface: 76C to 76D. Mature, lower surface: 76A to 76D.

*Disc florets.*—Shape: Tubular with five lobes. Length: About 3 mm. Width: About 1 mm. Texture: Sparse glandular hairs. Color: Immature: 154A. Mature: 7A. Number of disc florets per inflorescence: Numerous.

*Peduncle.*—Length: About 8.9 to 16.5 cm. Strength: Initially somewhat flexible becoming fairy rigid; erect. Texture: Smooth, glabrous. Color: 137A.

*Involucral bracts.*—Arrangement: Imbricate. Quantity: About 13 to 21 per inflorescence. Shape: Broadly oblong. Apex: Fringed. Margin: Entire to faintly fringed. Texture: Somewhat fleshy. Color: 138A with brownish apex, 182B.

*Androecium.*—Only present on disc florets. Stamen number: Five per disc floret. Anther shape: Oblong to linear. Anther color: 163C. Amount of pollen: Scarce. Pollen color: 13C.

*Gynoecium.*—Pistil number: One per floret. Stigma shape: Bilobate. Style length: About 3 mm. Style color: 151A. Stigma color: 151A.

Disease resistance: May be susceptible to Botrytis and fungal leaf spot diseases.

Seed production: Seed production has not been observed.

It is claimed:

1. A new and distinct cultivar of Brachycome plant named 'Jumbo Misty Lilac', as illustrated and described.

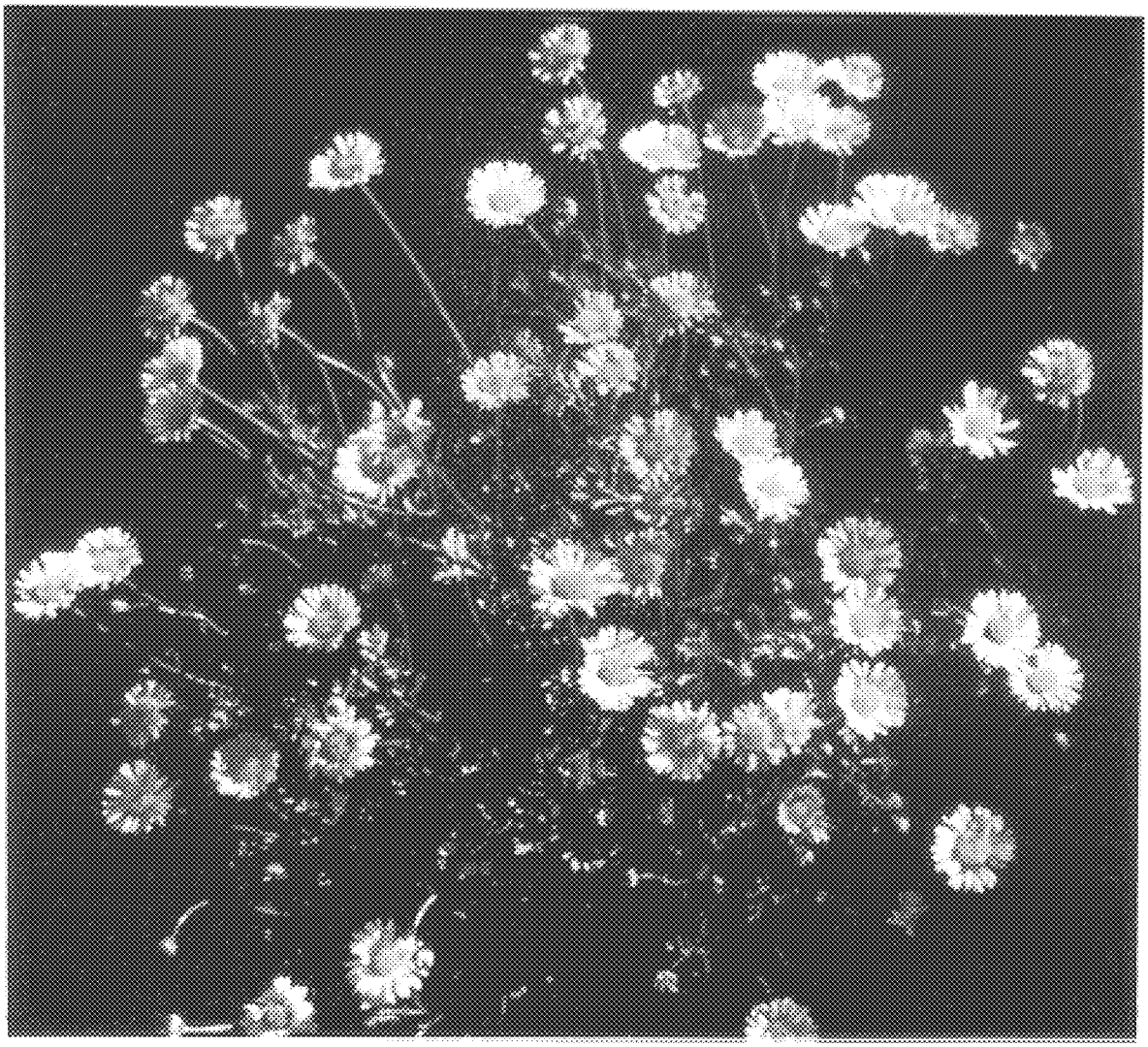

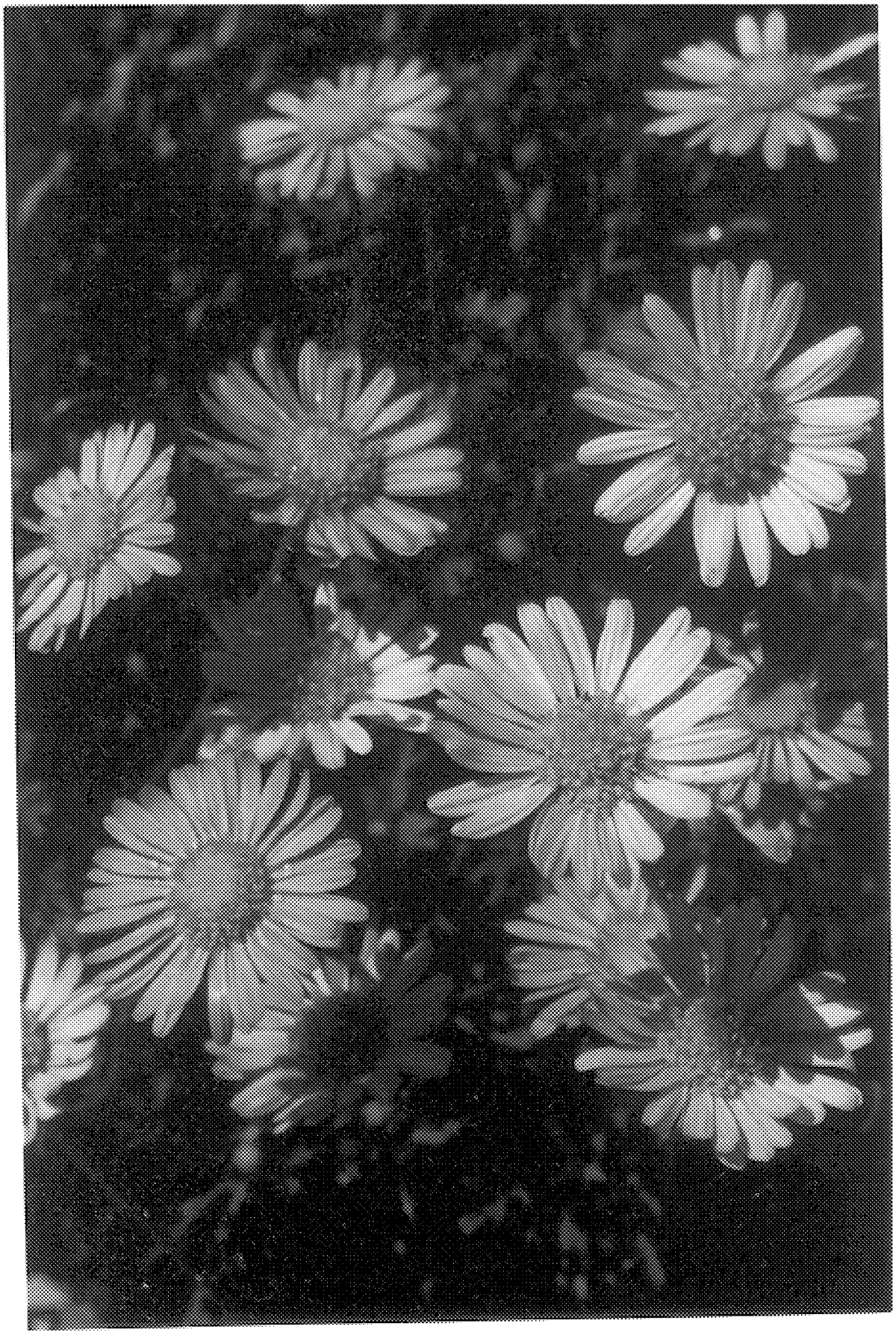

* * * * *